United States Patent [19]
Kappock et al.

[11] Patent Number: 5,939,203
[45] Date of Patent: *Aug. 17, 1999

[54] DISCOLORATION PREVENTION IN PYRITHIONE-CONTAINING COATING COMPOSITIONS

[75] Inventors: Paul S. Kappock, East Hampton; Patrick Flaherty, Waterbury, both of Conn.

[73] Assignee: Arch Chemicals, Inc., Cheshire, Conn.

[*] Notice: This patent is subject to a terminal disclaimer.

[21] Appl. No.: 08/804,225

[22] Filed: Feb. 21, 1997

Related U.S. Application Data

[60] Continuation-in-part of application No. 08/670,051, Jun. 25, 1996, Pat. No. 5,883,154, which is a division of application No. 08/383,122, Feb. 3, 1995, Pat. No. 5,562,995.

[51] Int. Cl.$^6$ ..................................................... B32B 15/04
[52] U.S. Cl. .................. 428/469; 106/18.33; 106/18.34; 106/18.36; 428/472
[58] Field of Search .................................... 428/469, 472; 106/18.33, 18.34, 18.36

[56] References Cited

U.S. PATENT DOCUMENTS

| | | |
|---|---|---|
| 2,809,971 | 10/1957 | Bernstein et al. . |
| 3,159,640 | 12/1964 | McClure et al. . |
| 4,161,526 | 7/1979 | Gorman . |
| 4,565,856 | 1/1986 | Trotz et al. ............................... 526/265 |
| 4,818,436 | 4/1989 | French et al. . |
| 4,957,658 | 9/1990 | French et al. . |
| 5,518,774 | 5/1996 | Kappock et al. ......................... 427/384 |
| 5,562,995 | 10/1996 | Kappock et al. ......................... 428/469 |

*Primary Examiner*—Mary E. Ceperley
*Attorney, Agent, or Firm*—Dale Lynn Carlson; Wiggin & Dana

[57] ABSTRACT

Disclosed is an aqueous coating composition comprising: (a) water, (b) a base medium, (c) a pyrithione salt, in an amount of from 0.01% to 2.0% based upon the weight of the composition, and (d) zinc oxide compound selected from the many grades suitable for paint manufacture at a concentration of from 0.001% to 10% based upon the weight of the coating composition. Also disclosed is an aqueous antimicrobial coating composition, characterized by antimildew efficacy and protected against discoloration attributable to the presence of pyrithione therein, said composition being selected from the group consisting of water-based paints, adhesives, caulks and sealants, and combinations thereof, said composition comprising water, a pyrithione salt or acid, an organic base medium and a zinc compound, said zinc ion being present in said composition in an amount of from 0.001% to 10% based upon the weight of the coating composition.

17 Claims, No Drawings

DISCOLORATION PREVENTION IN PYRITHIONE-CONTAINING COATING COMPOSITIONS

CROSS-REFERENCE TO RELATED APPLICATIONS

This application is a continuation-in-part of application Ser. No. 08/670,051, filed on Jun. 25, 1996, now U.S. Pat. No. 5,883,154 which is a division of application Ser. No. 08/383,122, filed on Feb. 3, 1995, now U.S. Pat. No. 5,562,995.

FIELD OF THE INVENTION

This invention relates generally to coating compositions, and, more specifically, to such compositions that are characterized by enhanced antimicrobial efficacy and resistance to discoloration, both in their wet state and, after drying, in the form of a dry film on a substrate.

BACKGROUND OF THE INVENTION

Pyrithiones are well-known antimicrobial additives that are useful in a myriad of applications. Sodium pyrithione (also called the sodium salt of 1-hydroxy-2-pyridinethione, sodium pyridine-2-thiol-N-oxide, or 2-pyridinethiol-1-oxide, Na salt) is one pyrithione salt having excellent antimicrobial properties, and is typically employed as a biocide and preservative in functional fluids, such as metalworking fluids, lubricants, cosmetics and toiletries. Sodium pyrithione is a well-known commercial product commonly made by reacting 2-chloropyridine-N-oxide with NaSH and NaOH, as disclosed, for example, in U.S. Pat. No. 3,159,640.

Likewise, zinc pyrithione [also known as zinc pyridine-2-thiol-N-oxide or bis [1-hydroxy-2(H) pyridinethionato]-zinc] is an excellent antimicrobial additive. Zinc pyrithione may be made by reacting 1-hydroxy-2-pyridinethione or a soluble salt thereof with a zinc salt (e.g., $ZnSO_4$) to form a zinc pyrithione precipitate, as disclosed, for example in U.S. Pat. No. 2,809,971. Zinc pyrithione has been employed as a broad-spectrum anti-microbial agent and preservative in metalworking fluids, plastics, paints, adhesives and cosmetics. Its principal uses are as an anti-dandruff agent in hair products, as a preservative in various cosmetics, and as an antifoulant in marine paints. The commercial use of zinc pyrithione in paints, adhesives, caulks and sealants is growing.

In the presence of ferric ion, sodium or zinc pyrithione-containing compositions tend to turn blue, even when the ferric ion is present in mere trace amounts, much less when higher amounts of the ferric ion is present. Likewise, in the presence of ultraviolet radiation, which is a component of natural, outdoor light, photodegradation of the pyrithione moiety may occur. This blue or yellow discoloration is undesirable for aesthetic reasons, as well as for functional reasons relating to unwanted color formulation.

Since the aesthetics of paints, adhesives, caulks and sealants normally require certain desirable colors after drying to form a dry coating on a substrate, and since the formulators of such products go to great lengths to achieve specific color effects, any ingredient which causes the formulation to vary much from a desired white or color may make the colorant formulators' task very difficult. For example, when formulating water-based paints, paint bases (i.e., the partially formulated paint before pigment addition), adhesives, caulks and sealants, any unwanted color in an additive can adversely affect the color of the formulated product, Such discoloration typically adversely affects the desired product color, producing an off-color product.

Likewise, yellowing of the dry coating film on a substrate, by virtue of ultraviolet ("uv") exposure as a component of natural outdoor light, adversely affects the paint in two respects. First, the yellowing of the paint is an aesthetic problem since the paint changes color upon uv exposure. Second, photodegradation of pyrithione attributable to uv exposure diminishes the amount of pyrithione available to protect the paint film.

In the past, various solutions to the blue discoloration problem have been proposed. By way of illustration, U.S. Pat. Nos. 4,957,658 and 4,818,436 disclose solutions to the above-discussed discoloration problem attributable to the presence of ferric ion plus pyrithione, in paints and functional fluids (e.g., metalworking fluids) respectively, by adding to the paint or functional fluid an alkali metal or alkaline earth metal salt of 1-hydroxyethane-1,1-diphosphonic acid. Although the '658 and '436 patents propose good solutions to the discoloration, these solutions are not always as cost effective or permanent as might be desired.

As another illustration, U.S. Pat. No. 4,161,526 discloses a white to cream yellow pyrithione, pyrithione salt or dipyrithione for application to skin or hair containing from about 0.01 percent to about 1 percent of the zinc salt of an organic carboxylic or inorganic acid, zinc hydroxide or zinc oxide, or a mixture thereof. The composition of the '526 patent is said to be effective in preventing or removing discoloration caused by formation of a colored pyrithione, pyrithione salt, or dipyrithione contaminant (said to be iron pyrithione) in the composition. The '526 patent does not teach a solution to the discoloration problem in compositions unrelated to skin or hair care, and not containing iron pyrithione.

In addition to the discoloration problem, unwanted ions, such as ferric ion, can cause a functional problem with respect to the antimicrobial performance of pyrithione. It is believed by the present inventors that this performance problem results from the fact that the pyrithione tends to form a blue precipitate in the presence of ferric ion, and precipitation of pyrithione reduces the amount of available pyrithione throughout the composition, thereby diminishing the biocidal protection thereof.

Moreover, the present inventors have found that the presence of a large amount of zinc oxide in a pyrithione-containing paint can surpress the short-term (or initial stage) of antimicrobial efficacy imparted by the pyrithione to the paint when dried to form a dry film on a substrate. This diminished short term efficacy adversely affects the performance of the paint, particularly in regard to resistance of the paint film to mildew growth.

New solutions to the yellow, blue and green discoloration problem in various pyrithione-containing aqueous coating compositions, particularly paints, adhesives, caulks and sealants would be highly desired. Preferred solutions would includes those that enable pyrithione to be utilized in coating compositions containing iron or copper, is without encountering any resulting discoloration of the composition, and that is cheaper, longer lasting, and/or uses lower levels of additives than required by the above-discussed prior art. A particularly preferred solution, namely one providing improved short-term and long-term antimicrobial resistance of the coating composition and resulting coating against microbial attack, would be highly desired by the paint, adhesives, caulks and sealants manufacturing community. The present invention provides one such solution.

SUMMARY OF THE INVENTION

In one aspect, the present invention relates to an aqueous coating composition comprising:
a) water,
b) a base medium,
c) a pyrithione salt, in an amount of from 0.01% to 2.0% based upon the weight of the composition, and
d) zinc oxide compound selected from the many grades suitable for paint manufacture at a concentration of from 0.001% to 10% based upon the weight of the composition. Typical coating compositions include aqueous compositions of a paint, adhesive, caulk, sealant, latex emulsion, pigment slurry, patching compound, joint compound, or concrete admixture.

In another aspect, the present invention relates to a process for inhibiting dry film-discoloration of a pyrithione-containing coating composition, attributable to ultraviolet light degradation of said pyrithione, which comprises incorporating into said coating composition an effective amount of a zinc compound selected from the group consisting of zinc salts of organic acids, zinc salts of inorganic acids, zinc hydroxide, zinc oxide, and combinations thereof.

In yet another aspect, the present invention relates to a process for removing an undesirable discoloration in an aqueous antimicrobial composition containing a dissolved metal ion selected from the group consisting of ferric ion, cupric ion, and combinations thereof, and containing pyrithione, which comprises contacting said composition with a zinc ion in a molar amount at least equal to the amount of said dissolved metal ion in said composition.

In still another aspect, the present invention relates to an aqueous antimicrobial coating composition, characterized by antimildew efficacy and protected against discoloration attributable to the presence of pyrithione therein, said composition being selected from the group consisting of water-based paints, adhesives, caulks and sealants, and combinations thereof, said composition comprising water, a pyrithione salt or acid, an organic base medium and a zinc compound, said zinc ion being present in said composition in an amount of from 0.001% to 10% based upon the weight of the coating composition.

In yet another aspect, the present invention relates to a coated substrate comprising a substrate selected from the group consisting of wood, metal, plastic substrates, and combinations thereof, and a coating on said substrate, said coating comprising pyrithione and a zinc compound selected from the group consisting of zinc salts of organic acids, zinc salts of inorganic acids, zinc hydroxide, zinc oxide, and combinations thereof These and other aspects will become apparent upon reading the following detailed description of the invention.

DETAILED DESCRIPTION OF THE INVENTION

It has now been surprisingly found in accordance with the present invention that the combination of a zinc compound (such as a zinc salt, zinc oxide or zinc hydroxide) together with a pyrithione compound (preferably zinc pyrithione) in a coating composition provides an advantageous combination of antimicrobial (particularly antimildew) efficacy and resistance to UV attack with respect to the dry coating made by applying the coating composition to a substrate.

It has also been surprisingly found in accordance with the present invention that the addition of zinc to a composition containing pyrithione and ferric or cupric ion reduces or avoids a discoloration problem otherwise attributable to such composition. Without wishing to be bound by any particular theory, there are multiple potential causes of the discoloration problem. For example, the presence of undesireable ions in tap water and "filler" components of the coating composition, such as iron ion, causes the formation of an insoluble iron pyrithione precipitate that not only discolors the composition, but also depletes the available pyrithione in sodium pyrithione-containing compositions, thereby diminishing the antimicrobial efficacy of the composition.

Additionally, ultraviolet radiation, a component of natural, outdoor light, tends to cause yellow discoloration of dry-film coatings containing pyrithione. It has now been found that the presence of zinc oxide within the preferred range of from 0.02% to 0.5% by weight, based upon the weight of the coating composition, in a pyrithione-containing coating composition contributes both to antimicrobial efficacy and avoidance of undesirable blueing or other discoloration of the coating composition, as well as avoidance of undesirable yellowing or other discoloration of the dry film resulting from the coating of a substrate with the coating composition.

The term "discoloration" as employed herein with respect to pyrithione-containing coating compositions is intended to describe any unacceptable gray, blue, black, purple, green, or color other than the natural color or desired artificial color of the paint or paint base formulation. The term "discoloration" is also intended to describe any yellow or brown discoloration of the dry film resulting from coating a substrate with the coating composition. Such yellow or brown discoloration is typically caused by photodegradation of pyrithione in the coating.

Discoloration of the coating composition can be attributable to unwanted metal ions (such as iron or copper) entering the coating composition from the starting materials employed in the preparation of the coating composition. Typical starting materials include tap water, and fillers (such as calcium carbonate) used to prepare coating compositions, as well as a source of pyrithione in the form of sodium pyrithione, zinc pyrithione, and combinations thereof. It is noted, for example, that the natural color of sodium pyrithione itself is a clear yellow. It is quite common, however, for iron and/or copper contaminants to be introduced into the aqueous composition from the tap water or fillers used in preparing the coating compositions, causing discoloration of the composition. One way of quantifying the extent of discoloration is by measuring the reflectance color parameters, and calculating a whiteness value from them. Another method is to visually inspect the composition for any signs of off-whiteness, as compared to the desired or white color.

In water-based paints, adhesives, caulks and sealants, significant levels of ferric or copper ion impurities in an amount of 250 ppm or higher are not uncommon. By incorporating an effective amount of the zinc salt of an organic acid or inorganic acid, zinc hydroxide or zinc oxide or a mixture thereof into the composition, the blue discoloration typically attributable to the presence of ferric ion bound with pyrithione is suitably reduced, eliminated or avoided, as is the green discoloration attributable to the presence of copper ion.

The amount of the above described zinc salt of an organic acid or inorganic acid, zinc hydroxide or zinc oxide, or combination thereof, needed to prevent discoloration in the coating composition in which it is employed, and the resulting dry film made by coating a substrate with the coating composition, can vary over a wide range of from 0.001% or lower to 10% or greater (advantageously from 0.001% to 3%, more advantageously from 0.02% to 0.5%), based upon the weight of the coating composition in which it is employed.

In order to provide an advantageous combination of short term and longer term antimicrobial efficacy in the dry film when using zinc oxide, it has now been found that the amount of zinc oxide preferably should not exceed 0.5% by weight (advantageously from 0.002% to 0.2%) based upon the weight of the coating composition. Above 0.5%, there is a risk that the zinc oxide will inhibit the short term efficacy of the zinc pyrithione in the dry film due the the well-known "common ion effect" attributable to the zinc present in both of these components. This "common ion effect" forces an equilibrium toward unionized zinc pyrithione where zinc ion, pyrithione ion, and unionized zinc pyrithione are all present in the composition, and the antimicrobial efficacy of zinc pyrithione is suppressed as long as this component remains in unionized form.

The pyrithione used in the process and composition of this invention is preferably a pyrithione salt, such as sodium pyrithione, zinc pyrithione, chitosan pyrithione, magnesium disulfide pyrithione, and the like, although pyrithione acid can be used if desired. More preferable pyrithione salts include sodium pyrithione, and zinc pyrithione, most preferably zinc pyrithione.

The sodium pyrithione useful in the present invention is a well-known commercial product that is commonly made by reacting 2-chloropyridine-N-oxide with NaSH and NaOH, as illustrated by the disclosures of U.S. Pat. No. 3,159,640.

Zinc pyrithione may be made by reacting 1-hydroxy-2-pyridinethione (i.e., pyrithione acid) or a soluble salt thereof with a zinc salt (e.g., $ZnSO_4$) to form a zinc pyrithione precipitate, as illustrated by the disclosures of U.S. Pat. No. 2,809,971.

The aqueous compositions of the present invention are suitable for a variety of uses, such as, for example as soap, shampoo, skin care medicaments, paint, or incorporated into or onto plastic or a woven or non-woven fibers, when formulated to contain the requisite components in addition to the antimicrobial component.

The antimicrobial compositions of the present invention are particularly useful in the form of paints, including indoor and outdoor household paints, industrial and commercial paints. In addition, the antimicrobial compositions provide desirable results when the antimicrobial component is incorporated into exterior paints of the latex types.

The coating compositions of the present invention are suitably applied to a substrate, such as a wood, plastic or metal substrate, and allowed to dry to form a dry coating.

The dry film formed by coating and drying the coating composition of the present invention onto a substrate exhibits excellent resistance to the growth of fungus and algae, as show by outdoor exposure tests using boards painted with the coating composition. However, it can be envisioned that certain paint formulations, namely those that are rich in hydrophilic components, might provide an environment that is more favorable to the growth of both mildew and algae, as compared to the coatings tested. Mildew needs moisture to survive. Hydrophilic materials in a paint film will keep the moisture level of the film higher. This provides a better environment for mildew and also may contribute to accelerated leaching out of hydrophilic materials. The hydrophilic components in these formulations tend to cause relatively soluble antimicrobial additives to leach out of the formulation, thus providing good short-term antimicrobial protection at the expense of longer-term antimicrobial protection due to this leaching effect. Under these circumstances, it is envisioned, in accordance with the present invention, that the use of zinc pyrithione, a relatively water-insoluble antimicrobial additive, in combination with a relatively water-soluble antimicrobial additive provides an excellent combination of desired short-term and long-term antimicrobial protection in dry paint films made using paint formulations containing high levels of hydrophilic components. Relatively water-soluble antimicrobials that are useful as co-biocides for dry-film efficacy when used in combination with zinc pyrithione in accordance with the present invention include iodopropynyl butylcarbamate ("IPBC"), n-octyl isothiazolin-one ("OIT"), methylene thiocyanate ("MTC"), thiocyanomethylthio benzothiazole ("TCMTB"), thiazolyl benzimidazole ("TBZ"), benzimidazolyl carbamic acid methylester ("BCM"), triazoles, such as chlorophenylethyl dimethylethyl triazole ethanol ("Tebuconazole", commercially available from Bayer), substituted triazines such as tert-butylamino cyclopropylamino methylthio-s-triazine, and dichlorophenyl dimethylurea ("Diuron", commercially available from Bayer), as well as combinations thereof. These cobiocides are suitably added either alone, or in admixture with zinc pyrithione, to the desired paint, to provide a paint containing a molar ratio of zinc pyrithione to co-biocide of from 1:10 to 10:1.

Typically a paint composition will contain, in addition to the antimicrobial component, a resin, a pigment, and various optional additives such as thickening agent(s), wetting agents and the like, as is well known in the art. The resin is preferably selected from the group consisting of vinyl, alkyd, epoxy, acrylic, polyurethane and polyester resins, and combinations of thereof. The resin is preferably employed in an amount of between about 20% and about 80% based upon the weight of the paint or paint base.

In addition, the paint composition of the present invention optionally additionally contains optional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally occurring or synthetic clays, such as kaolin, montomorillonite, and bentonite), clay mica (muscovite), and chlorite (hectonite), and the like. In addition to clays other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative, thickening agents include cellulose derivatives, for example methyl, hydroxyethyl, hydroxypropyl and carboxymethyl cellulose, poly(vinyl alcohol), poly (vinylpyrolidone), poly(ethyleneglycol), salts of poly (acrylic acid) and salts of acrylic acid/acrylamide copolymers.

Suitable wetting and dispersing agents include sodium polyphosphate, salts of low molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer 1.2-diols for example glycol, propylene glycol (1.2) and butylene glycol 1.2) or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation of the paint composition may be reduced by adding solvents, such as ethylene glycol, butyl glycol, ethyl glycol acetate, ethyl diglycol acetate, butyl diglycol acetate, or alkylated aromatic hydrocarbons. As defoaming agents there are suitable for example poly(propylene glycol) and polysiloxanes. Optionally other biocides can additionally be incorporated into the paint formulations of the present invention.

The paint composition of the present invention may be used as a paint for natural or synthetic materials, for example wood, paper, metals, textiles and plastics. It is particularly suitable as an outdoor paint, and is excellent for use as a marine paint.

Another significant use for the aqueous composition of the present invention is as a latex tile adhesive typically containing, for example, in addition to the antimicrobial component, a latex emulsion, an optional rosin emulsion, an optional As plasticizer, an optional antioxidant, and an optional pigment or filler (such as calcium carbonate). Yet another significant use for the aqueous composition of the present invention is as a latex caulk, typically containing, in addition to the antimicrobial component, an acrylic latex, a nonionic surfactant, a dispersant, an optional plasticizer, and an optional pigment or filler (such as calcium carbonate).

The aqueous antimicrobial compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi on various substrates, and can be applied to bacterial or fungal organisms or on substrates in an antimicrobial amount by conventional procedures such as spraying, dipping, drenching impregnation, and the like.

The invention is further illustrated by the following Examples. Unless otherwise stated, the "parts" and "%" are "parts by weight" and "percent by weight", respectively.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

The following examples are intended to illustrate, but in no way limit the scope of, the present invention.

Comparative Example A

Efficacy of Zinc Oxide as an Antimicrobial Against Mildew in an Acrylic Latex House Paint In order to test the effectiveness of zinc oxide as an anti-mildew additive in a latex house paint, the following experiment was conducted. A paint was prepared having the following composition:

| Latex Paint Formulation Containing Zinc Oxide | |
| --- | --- |
| Ingredient | Grams |
| Water | 240.0 |
| Hydroxyethyl Cellulose | 6.0 |
| Tamol 960 1 | 6.2 |
| Ethylene Glycol | 50.0 |
| Colloid 643 2 | 2.0 |
| Triton ® CF-103 | 5.0 |
| Potassium Tripolyphosphate | 3.0 |
| Pigment grind: | |
| Titanium Dioxide (Rutile) | 500.0 |
| Aluminum Magnesium Silicate | 335.0 |
| Attapulgite Clay | 6.0 |
| Zinc Oxide | 12.0 |
| Aluminum Silicate | 47.0 |
| Propylene Glycol | 68.0 |
| Let Down: | |
| Water | 201.0 |
| Acrylic Latex Emulsion 60.0% solids | 760.0 |
| Colloid 643 | 6.0 |
| Texanol ® 4 | 22.0 |
| Hydroxyethyl Cellulose 2.5% in water | 80.0 |
| Ammonia | 0.5 |
| Total Mass in Grams | 2349.7 |

The paint was applied by brush in two coats to an unprimed white pine substrate to determine whether the coating supported the growth of mildew on the coating. After four months of outdoor aging, the growth was rated in accordance with the procedure of ASTM D 3274-82 to a rating of 6 (moderate growth).

Comparative Example B

Efficacy of Zinc Pyrithione in an Acrylic Latex House Paint

As another test of the effectiveness of zinc oxide as an anti-mildew additive in a latex house paint, the following experiment was conducted. A paint was prepared having the following composition:

| Latex Paint Formulation Containing Zinc Pyrithione and No Zinc Oxide | |
| --- | --- |
| Ingredient | Grams |
| Water | 240.0 |
| Hydroxyethyl Cellulose | 6.0 |
| Tamol 960 1 | 6.2 |
| Ethylene Glycol | 50.0 |
| Colloid 643 2 | 2.0 |
| Triton ® CF-10 3 | 5.0 |
| Potassium Tripolyphosphate | 3.0 |
| Pigment Grind: | |
| Titanium Dioxide (Rutile) | 500.0 |
| Aluminum Magnesium Silicate | 335.0 |
| Attapulgite Clay | 6.0 |
| Zinc Pyrithione 48% Dispersion | 24.0 |
| Aluminum Silicate | 47.0 |
| Propylene Glycol | 68.0 |

-continued

Latex Paint Formulation Containing Zinc Pyrithione and No Zinc Oxide

| Ingredient | Grams |
|---|---|
| Let Down: | |
| Water | 201.0 |
| Acrylic Latex Emulsion 60.0% solids | 760.0 |
| Colloid 643 | 6.0 |
| Texanol ® 4 | 22.0 |
| Hydroxyethyl Cellulose 2.5% in water | 80.0 |
| Ammonia | 0.5 |
| Total Mass in Grams | 2361.7 |

The paint was applied by brush in two coats to an unprimed white pine substrate to determine whether the coating supported the growth of mildew on the coating. After four months of outdoor aging, the growth was rated in accordance with the procedure of ASTM D 3274-82 to a rating of 8 (light growth).

EXAMPLE 1
Efficacy of Zinc Pyrithione and Zinc Oxide in a Acrylic Latex House Paint In order to test the effectiveness of the combination of zinc oxide and zinc pyrithione as a combination of anti-mildew additives in a latex house paint, the following experiment was conducted. A paint was prepared having the following composition:

Latex Paint Formulation Containing Zinc Pyrithione and Zinc Oxide

| Ingredient | Grams |
|---|---|
| Water | 240.0 |
| Hydroxyethyl Cellulose | 6.0 |
| Tamol 960 1 | 6.2 |
| Ethylene Glycol | 50.0 |
| Colloid 643 2 | 2.0 |
| Triton ® CF-10 3 | 5.0 |
| Potassium Tripolyphosphate | 3.0 |
| Pigment Grind: | |
| Titanium Dioxide (Rutile) | 500.0 |
| Aluminum Magnesium Silicate | 335.0 |
| Attapulgite Clay | 6.0 |
| Zinc Pyrithione 48% Dispersion | 18.0 |
| Zinc Oxide | 3.0 |
| Aluminum Silicate | 47.0 |
| Propylene Glycol | 68.0 |
| Let Down: | |
| Water | 201.0 |
| Acrylic Latex Emulsion 60.0% solids | 760.0 |
| Colloid 643 | 6.0 |
| Texanol ® 4 | 22.0 |
| Hydroxyethyl Cellulose 2.5% in water | 80.0 |
| Ammonia | 0.5 |
| Total Mass in Grams | 2361.7 |

Footnotes
1 An anionic dispersant, a product of Rohm and Haas Company
2 A defoamer, a product of Rhone-Poulenc Corp.
3 A nonionic surfactant, a product of Union Carbide Corp.
4 A coalescent, a product of Eastman Kodak Company The paint was applied by brush in two coats to an unprimed white pine substrate to determine whether the coating supported the growth of mildew on the coating. After four months of outdoor aging, the growth was rated in accordance with the procedure of ASTM D 3274-82 to provide a rating of 10 (no growth).

All three of the paints from the above three examples (Comparative Examples A and B and Example 1) were painted on three different sections of the same pine board to minimize the effect of using different pieces of wood. Example 1 demonstrates that the combination of zinc pyrithione and zinc oxide suitably provides total resistance to the growth of mildew on painted wood substrates, whereas zinc oxide or zinc pyrithione alone (Comparative Examples A and B) does not provide such resistance.

EXAMPLE 2
Efficacy of Zinc Oxide in Avoiding Yellow Discoloration Caused by Exposure to Ultraviolet Light in Pyrithione Containing Paint Bases In order to test the effectiveness of zinc oxide in avoiding, eliminating or reducing yellow discoloration caused by ultraviolet in a pyrithione-containing paint, the following experiment was conducted.

Two samples of an aqueous latex paint formulation (below) containing zinc pyrithione and one not containing zinc pyrithione were applied to a panel and exposed in a QUV weatherometer for 500 hours. The yellowness index ("YI") was measured at time zero and after 500 hours of exposure. The difference in YI for the paint without zinc pyrithione after 500 hours of exposure was an increase in yellowness of 1.34. The difference in YI for the paint with 0.3% by weight of active zinc pyrithione was an increase of 3.68, indicating an increase in yellowing on exposure to UV with the paint containing zinc pyrithione.

To samples of each of these paints, 0.5% of zinc oxide was added. The difference in YI for the paint without zinc pyrithione was an increase 0.37 after 500 hours of exposure in a QUV weatherometer. The difference in YI for the paint that contained zinc pyrithione was 0.19 after 500 hours of exposure. This result demonstrates that zinc oxide will prevent the development of yellow color in a paint that contains zinc pyrithione when the paint is exposed to ultraviolet light.

Latex Paint Formulation with and without pyrithione

| Ingredient | A | | B |
|---|---|---|---|
| Water | 103.0 | grams | 103.0 |
| Hydroxyethyl Cellulose | 2.5 | grams | 2.5 |
| Tamol 9601 | 12.90 | | 12.9 |
| Ethylene Glycol | 18.00 | | 18.0 |
| Colloids 643 2 | 2.0 | | 2.0 |
| Nuosept 95 | 3.00 | | 3.0 |
| Potassium Tripolyphosphate | 2.0 | | 2.0 |
| Pigment Grind: | | | |
| Titanium Dioxide (Rutile) | 200.0 | | 200.0 |
| Sodium Potassium Aluminum Silicate | 225.0 | | 225.0 |
| Attapulgite Clay | 4.0 | | 4.0 |
| Let Down: | | | |
| Water | 50.0 | | 50.0 |
| Acrylic Latex Emulsion 63.0% solids | 260.0 | | 260.0 |
| Colloids 643 | 4.0 | | 4.0 |
| Texanol ® 3 | 12.0 | | 12.0 |
| Hydroxyethyl Cellulose 2.5% in water | 132.0 | | 132.0 |
| Ammonia | 1.0 | | 1.0 |
| Zinc Pyrithione 48% Dispersion | | | |
| Total Mass in Grams | 1031.4 | | 1037.4 |

To 200 grams of both A and B, 2.00 grams of a 50% zinc oxide dispersion was added for comparing the yellowing of paints with and without zinc pyrithione as summarized on page 23 lines 3–10.

EXAMPLE 3
Efficacy of Reduced Amounts Zinc Oxide in Avoiding Yellow Discoloration Caused by Exposure to Ultraviolet Light in Pyrithione Containing Paint Bases To determine if a lower concentration of zinc oxide could be used to provide effectiveness in avoiding, eliminating or reducing yellow discoloration caused by ultraviolet in a pyrithione-containing paint, the following experiment was conducted. Following the procedure of Example 2, two paints were prepared as follows: to Example 2 were prepared as follows:

| Ingredient | A | | B |
|---|---|---|---|
| Water | 103.0 | grams | 103.0 |
| Hydroxyethyl Cellulose | 2.5 | grams | 2.5 |
| Tamol 9601 | 12.90 | | 12.9 |
| Ethylene Glycol | 18.00 | | 18.0 |
| Colloids 643 2 | 2.0 | | 2.0 |
| Nuosept 95 | 3.00 | | 3.0 |
| Potassium Tripolyphosphate | 2.0 | | 2.0 |
| Pigment Grind: | | | |
| Titanium Dioxide (Rutile) | 200.0 | | 200.0 |
| Sodium Potassium Aluminum Silicate | 225.0 | | 225.0 |
| Attapulgite Clay | 4.0 | | 4.0 |
| Zinc Oxide | 2.0 | | 6.0 |
| Let Down: | | | |
| Water | 50.0 | | 50.0 |
| Acrylic Latex Emulsion 63.0% solids | 260.0 | | 260.0 |
| Colloids 643 | 4.0 | | 4.0 |
| Texanol ® 3 | 12.0 | | 12.0 |
| Hydroxyethyl Cellulose 2.5% in water | 132.0 | | 132.0 |
| Ammonia | 1.0 | | 1.0 |
| Zinc Pyrithione 48% Dispersion | 6.0 | | 6.0 |
| Total Mass in Grams | 1045.4 | | 1049.4 |

Footnotes
1 An anionic dispersant, a product of Rohm and Haas Company
2 A defoamer, a product of Rhone-Poulenc Corp.
3 A coalescent, a product of Eastman Kodak Company Films from these paints were exposed in a QUV weatherometer for 72 hours of continuous light with UVA 340 bulbs. The YI index was measured at that time and the difference from the YI at time zero was as follows:

| | YI |
|---|---|
| Paint Sample A | 1.35 |
| Paint Sample B | 0.76 |

The results provided in this example demonstrate that less than 0.2% of zinc oxide in the formulation will result in a reduction in yellowing caused by UV exposure. Adding an additional 0.4% zinc oxide for a total of 0.6% by weight resulted in an even greater reduction of UV induced yellowing.

EXAMPLE 4
Elimination of Blue Discoloration Caused by the Presence of Pyrithione and Ferric Ion In a Paint Base Efficacy of zinc oxide in eliminating blue coloration caused by the presence of ferric ion in sodium pyrithione containing paint bases.

In order to test the effectiveness of zinc oxide in eliminating or reducing blue color caused by ferric ion in a pyrithione-containing paint, the following experiment was conducted.

Two samples weighing 150 grams each of below aqueous (latex) paint formulation containing sodium pyrithione and zinc oxide were placed in plastic cups. A wooden tongue depressor was then dipped into each sample and then allowed to dry to provide a control or "blank" comparison. Ferric chloride was then added to each sample to provide a concentration of 64 ppm of ferric ion in each sample. Tongue depressor coatings were taken to provide a basis for comparison. No discoloration formed in the paints themselves or the dry films of the painted tongue depressor.

Latex Paint Formulation Containing Sodium Pyrithione and Zinc Oxide

| Ingredient | Grams |
|---|---|
| water | 240.00 |
| hydroxyethyl cellulose | 6.0 |
| Tamol 850[1/] | 14.2 |
| Ethylene Glycol | 50.0 |
| Colloid 643[2/] | 2.0 |
| Triton ® CF-10[3/] | 5.0 |
| sodium pyrithione 40% active | 3.0 |
| potassium tripolyphosphate | 3.0 |
| Pigment grind: | |
| titanium dioxide (Rutile) | 424.0 |
| aluminum magnesium silicate | 228.0 |
| attapulgite clay | 3.0 |
| zinc oxide | 50.0 |
| aluminum silicate | 100.0 |
| propylene glycol | 68.0 |
| Let Down: | |
| water | 84.0 |
| acrylic latex emulsion 58.0% solids | 700.0 |
| Colloid 643 | 6.0 |
| Texanol ® [4/] | 18.6 |
| hydroxyethyl cellulose 2.5% in water | 236.4 |
| Total Mass in Grams | 2241.2 |

[1/]An anionic dispersant, a product of Rohm and Haas Company
[2/]A defoamer, a product of Rhone-Poulence Corp.
[3/]A nonionic surfactant, a product of Union Carbide Corp.
[4/]A coalescent, a product of Eastman Kodak Company Next, as a comparison, two samples weighing 150 grams each of below aqueous (latex) paint formulation containing sodium Pyrithione and no zinc oxide were placed in paper cups. A wooden tongue depressor was then dipped into each sample and then allowed to dry to provide a control or "blank" comparison. Ferric chloride was then added to each sample to provide a concentration of 64 ppm of ferric ion in each sample. The comparison coatings on the tongue depressor were visually observed to provide a basis for the comparison. After 30 minutes a bluish gray discoloration formed in the paints themselves and the dry films of the painted tongue depressor.

Latex Paint Formulation Containing Sodium Pyrithione and Zinc Oxide

| Ingredient | Grams |
|---|---|
| water | 240.00 |
| hydroxyethyl cellulose | 6.0 |
| Tarnol 850[5/] | 14.2 |
| Ethylene Glycol | 50.0 |
| Colloid 643[6/] | 2.0 |
| Triton ® CF-10[7/] | 5.0 |
| sodium pyrithione 40% active | 3.0 |
| potassium tripolyphosphate | 3.0 |
| Pigment grind: | |
| titanium dioxide (Rutile) | 424.0 |
| aluminum magnesium silicate | 228.0 |
| attapulgite clay | 3.0 |
| aluminum silicate | 100.0 |
| propylene glycol | 68.0 |
| Let Down: | |
| water | 84.0 |
| acrylic latex emulsion 58.0% solids | 700.0 |

| Latex Paint Formulation Containing Sodium Pyrithione and Zinc Oxide | |
|---|---|
| Ingredient | Grams |
| Colloid 643 | 6.0 |
| Texanol ® [8/] | 18.6 |
| hydroxyethyl cellulose 2.5% in water | 236.4 |
| Total Mass in Grams | 2191.2 |

[5/]An anionic dispersant, a product of Rohm and Haas Company
[6/]A defoamer, a product of Rhone-Poulence Corp.
[7/]A nonionic surfactant, a product of Union Carbide Corp.
[8/]A coalescent, a product of Eastman Kodak Company

EXAMPLE 5
Elimination of Blue Discoloration Caused by the Presence of Pyrithione and Ferric Ion In a Paint Efficacy of zinc oxide in eliminating blue coloration caused by the presence of ferric ion in zinc pyrithione containing paint.

In the presence of ferric ion, zinc pyrithione-containing paint compositions also tended to turn blue to gray, although at a much slower rate than did the sodium pyrithione-containing paints. 48 percent aqueous zinc pyrithione was added to a white paint which contained 1.0 percent zinc oxide to provide a level of 3000 ppm of zinc pyrithione in the sample. Ferric chloride was then added to provide a concentration of 64 ppm of ferric ion in the sample. Upon standing for a month, the paint was found to have no discoloration.

When this composition is painted over bare steel or copper, no discoloration is detected. This result is surprising, since the copper would have been expected to turn the paint a greenish color, and the steel would have been expected to turn the paint a bluish color.

As a comparison, 48 percent aqueous zinc pyrithione is added to a white paint containing no zinc oxide to provide a level of 3000 ppm of zinc pyrithione in the sample. Ferric chloride is then added to provide a concentration of 64 ppm of ferric ion in the sample. Upon standing for a week, the paint is found to turn bluish in color.

EXAMPLE 6
Process for the Removal of Discoloration Caused by the Presence of Pyrithione and Ferric Ion in Water-based Coatings 48 percent aqueous zinc pyrithione was added to a white paint sample to provide a level of 3000 ppm of zinc pyrithione in the sample. Ferric chloride was then added to provide a concentration of 25 ppm of ferric ion in the sample. Upon standing for two days, the paint was found to turn bluish in color. To this point 0.007 percent (70 ppm) of zinc sulfate was added and the paint was mixed for 5 minutes. After sitting for an additional 5 minutes it was observed that the paint had whitened and the bluish color was no longer noticeable. The addition of the zinc sulfate to this paint had removed the blue color which was formed from the addition of zinc pyrithione and ferric chloride.

What is claimed is:

1. An aqueous coating composition being a paint comprising:
   a) water,
   b) a base medium being a resin selected from the group consisting of vinyl, alkyd, epoxy, acrylic, polyurethane, polyester resins, and combinations thereof,
   c) a pyrithione salt, in an amount of from 0.01% to 2.0% based upon the weight of the composition, and
   d) zinc oxide compound selected from the many grades suitable for paint manufacture at a concentration of from 0.001% to 10% based upon the weight of the coating composition.

2. The coating composition of claim 1 wherein said zinc oxide is present in an amount of from 0.001% to 3%, based upon the weight of the coating composition.

3. The coating composition of claim 1 wherein said zinc oxide is present in an amount of from 0.02% to 0.5%, based upon the weight of the coating composition.

4. The coating composition of claim 1 wherein said zinc oxide is present in an amount of from 0.002% to 0.2%, based upon the weight of the coating composition.

5. The coating composition of claim 1 wherein said coating composition comprises a polymer latex.

6. The coating composition of claim 1 which additionally contains a co-biocide selected from the group consisting of iodopropynyl butylcarbamate ("IPBC"), n-octyl isothiazolin-one ("OIT"), methylene thiocyanate ("MTC"), thiocyanomethylthio benzothiazole ("TCMTB"), thiazolyl benzimidazole ("TBZ"), benzimidazolyl carbamic acid methylester ("BCM"), triazoles, substituted triazines, dichlorophenyl dimethylurea, and combinations thereof.

7. A process for inhibiting dry film-discoloration of a pyrithione-containing coating composition being a paint comprising a resin selected from the group consisting of vinyl, alkyd, epoxy, acrylic, polyester resins, and combinations thereof, said discoloration being attributable to ultraviolet light degradation of said pyrithione, which comprises incorporating into said coating composition an effective amount of a zinc compound selected from the group consisting of zinc salts of organic acids, zinc salts of inorganic acids, zinc hydroxide, zinc oxide, and combinations thereof, said zinc compound being employed in said coating composition in an amount of from 0.001% to 10% based upon the weight of the coating composition.

8. The process of claim 7 wherein said zinc compound is employed in said coating composition in an amount of from 0.001% to 3%, based upon the weight of the coating composition.

9. The process of claim 7 wherein said zinc compound is employed in said coating composition in an amount of from 0.02% to 0.5%, based upon the weight of the coating composition.

10. The process of claim 7 wherein said zinc compound is selected from the group consisting of zinc oxide, zinc hydroxide, zinc acetate, zinc sulfate, zinc chloride, and combinations thereof.

11. A process for removing an undesirable discoloration in an aqueous antimicrobial composition being a paint comprising a resin selected from the group consisting of vinyl, alkyd, epoxy, acrylic, polyester resins, and combinations thereof, said composition containing a dissolved metal ion selected from the group consisting of ferric ion, cupric ion, and combinations thereof, and containing pyrithione, which comprises contacting said composition with a zinc ion in a molar amount at least equal to the amount of said dissolved metal ion in said composition, wherein said amount of said zinc ion is between 100 ppm and 10,000 ppm in said composition.

12. The process of claim 11 wherein said zinc ion provided by incorporating into said composition a zinc compound selected from the group consisting of zinc salts of organic acids, zinc salts of inorganic acids, zinc hydroxide, zinc oxide, and combinations thereof.

13. The process of claim 11 wherein said zinc compound is selected from the group consisting of zinc acetate, zinc sulfate, zinc chloride, and combinations thereof.

14. An aqueous antimicrobial coating composition, characterized by antimildew efficacy and protected against discoloration attributable to the presence of pyrithione therein, said composition being selected from the group consisting of water-based paints, adhesives, caulks and sealants, and combinations thereof, said composition comprising water, a pyrithione salt or acid, an organic base medium and a zinc compound, said zinc compound being present in said composition in an amount of from 0.001% to 10% based upon the weight of the coating composition.

15. The coating composition of claim 14 wherein said zinc compound is present in an amount of from 0.001% to 3% based upon the weight of the coating composition.

16. A coated substrate comprising a substrate selected from the group consisting of wood, metal, plastic substrates, and combinations thereof, and a coating on said substrate, said coating comprising pyrithione and a zinc compound selected from the group consisting of zinc salts of organic acids, zinc salts of inorganic acids, zinc hydroxide, zinc oxide, and combinations thereof, wherein said zinc compound is present in said coating in an amount of from 0.001% to 10%, based upon the weight of the coating composition.

17. The coated substrate of claim 16 wherein said zinc compound is present in said coating in an amount of from 0.001% to 3%, based upon the weight of the coating.

* * * * *